United States Patent [19]
Adams

[11] Patent Number: 6,031,610
[45] Date of Patent: *Feb. 29, 2000

[54] MULTI-LOBE PUMP FOR PARTICLE COUNTERS

[75] Inventor: Craig D. Adams, Medford, Oreg.

[73] Assignee: Pacific Scientific Instruments Company, Grants Pass, Oreg.

[ * ] Notice: This patent issued on a continued prosecution application filed under 37 CFR 1.53(d), and is subject to the twenty year patent term provisions of 35 U.S.C. 154(a)(2).

[21] Appl. No.: 08/944,670

[22] Filed: Oct. 6, 1997

[51] Int. Cl.⁷ .................................................. G01N 21/53
[52] U.S. Cl. ............................................................. 356/339
[58] Field of Search ................................ 356/339; 418/19

[56] References Cited

U.S. PATENT DOCUMENTS

| | | | |
|---|---|---|---|
| 4,165,209 | 8/1979 | Eiermann | 418/190 |
| 4,215,977 | 8/1980 | Weatherston | 418/1 |
| 4,638,570 | 1/1987 | Soeters | 33/562 |
| 4,746,215 | 5/1988 | Gross | 356/339 |
| 4,768,934 | 9/1988 | Soeters | 418/1 |
| 4,781,541 | 11/1988 | Sohler et al. | 417/312 |
| 4,798,465 | 1/1989 | Knollenberg | 356/336 |
| 5,039,289 | 8/1991 | Eiermann et al. | 418/190 |
| 5,092,675 | 3/1992 | Sommer | 356/338 |
| 5,320,508 | 6/1994 | Kiefer | 418/206 |
| 5,600,438 | 2/1997 | Kreikebaum et al. | 356/339 |

*Primary Examiner*—Richard A. Rosenberger
*Attorney, Agent, or Firm*—Stoel Rives LLP

[57] ABSTRACT

A pump establishes gas flow in a particle counter. A pair of shafts having lobes is mounted in a first housing and serves to establish a gas flow path through a second housing which defines a view volume where particles are counted by light scattering or obscuration of a beam intersecting the light flow path. The lobes of the first housing do not contact each other or the walls of the housing, thereby limiting particles to those suspended in the gas flow.

15 Claims, 4 Drawing Sheets

MULTI-LOBE PUMP FOR PARTICLE COUNTERS

TECHNICAL FIELD

The invention relates to apparatus used in instruments for detecting, counting or measuring particles in a gas stream, particularly air. More specifically, the invention relates to an improved gas flow system in particle counters.

BACKGROUND ART

A typical prior art counter for particles suspended in a fluid is disclosed in U.S. Pat. No. 4,746,216 to K. Gross, assignor to Pacific Scientific Company. This patent describes a particle counter in which gas flows through a space within an enclosure, known as a view volume, monitored by a laser beam. The beam intersects the gas flow and illuminates particles flowing through the view volume. Light obscured by the particles, or scattered by the particles, is detected by an electronic detector sensitive to the obscuration or scattering of light. The resultant electrical signals are interpreted as particle counts.

The need for improved particle counters is largely driven by the semiconductor manufacturing industry. Silicon wafers have become larger in size while, at the same time, line widths and features on chips laid out on the wafer have become smaller. Chip size has become larger with more complex functions on each chip. Defects and particles which previously caused little harm now can render a large portion of a wafer useless. Thus, the role of small particles becomes increasingly important in monitoring quality of chip production. Air quality in clean rooms is especially critical at many stages of chip production. Semi-conductor companies routinely monitor air quality at all stages of chip production.

While various improvements have been made to particle counters themselves, including the optics, nozzle characteristics, lasers and laser cavities, detector attributes and signal electronics, little attention has been paid to the pumps which are used to maintain the air flow through the air through the view volume. Typically, pumps used in prior art particle counters use pistons, diaphragms or vanes to move a fluid carrier medium, such as air. Such pumps move relatively large volumes of the carrier medium at low cost. However, most prior art pumps are noisy, generate heat, and are somewhat inefficient. An object of the invention was to provide an improved pump for a particle counter which provides for quiet operation, relatively cool running and is efficient at flow rates and pressures used in particle counters.

SUMMARY OF THE INVENTION

The above object has been achieved in a particle counter having a flow of sample gas through a flow cell propelled by a pump of the lobe type. The number of lobes may vary. Where twin rotors have more than one lobe, the lobes are-interleaving. In the case where rotors have a single lobe, the lobes are cam-shaped. The interleaving lobes are typical of Roots pumps, frequently used in the automotive industry in superchargers. A motor drives the shafts carrying the rotors using a controller provided with feedback from a flowmeter so that a desired air volume may be pumped through the gas flow cell. The interleaving rotors are quiet, efficient and do not introduce particles because clearance is maintained between interleaving rotors and with surrounding walls.

BEST MODE OF CARRYING OUT THE INVENTION

Figure 1:
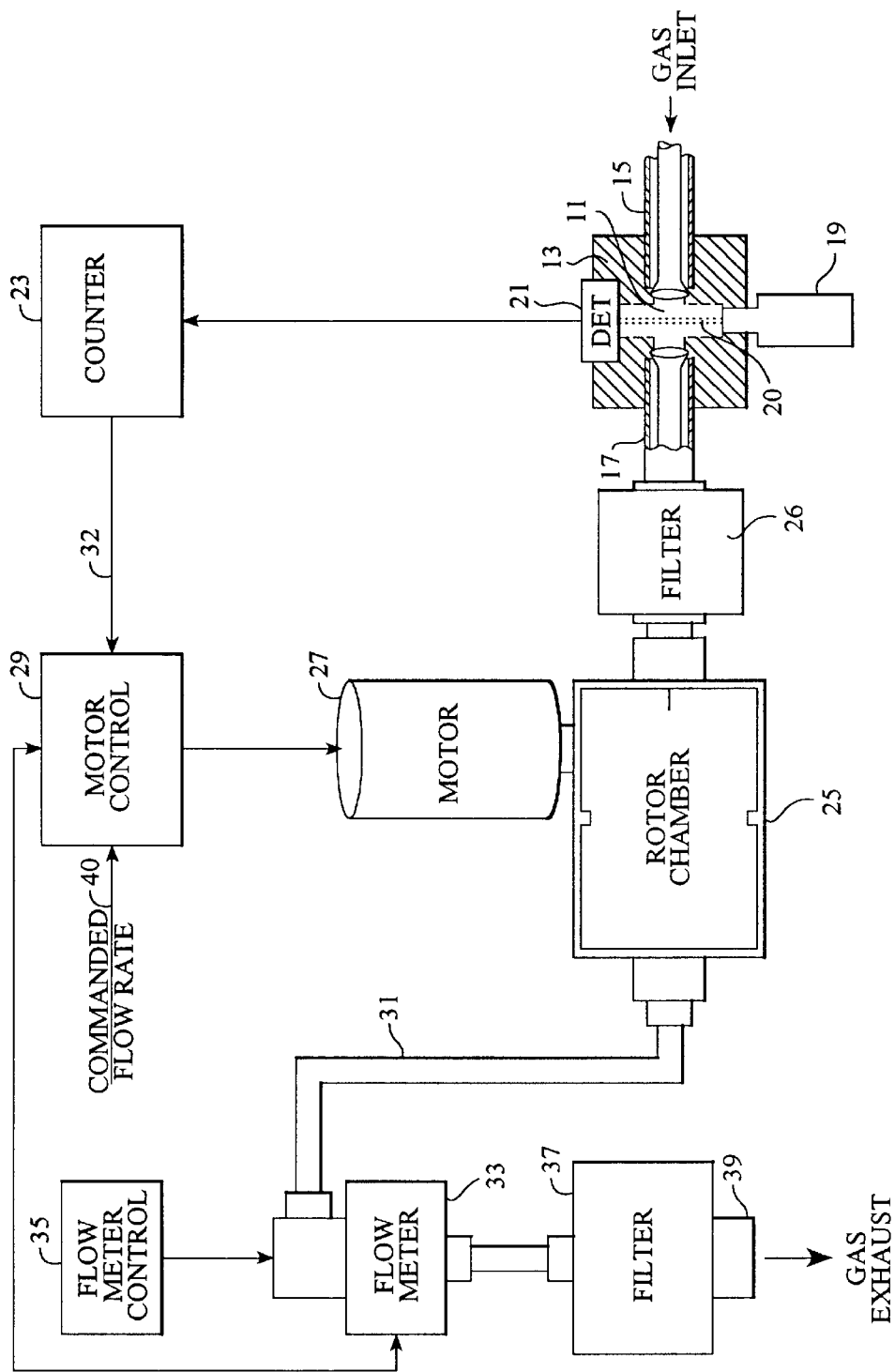
FIG. 1 is a block diagram plan of the apparatus of the present invention.

With reference to FIG. 1, a particle view volume 11, within a gas flow cell, is defined within a housing 13, which may be a block of metal or other material which does not generate particles. A first of two intersecting bores accommodates a gas inlet port 15 which faces a gas outlet port 17. A second orthogonal bore seats laser 19 which directs a beam 20 toward detector 21, intersecting the gas flow stream between gas inlet port 15 and gas outlet port 17.

The beam 20 illuminates individual particles flowing from the gas inlet port 15 to the gas outlet port 17 within the gas flow cell. The illuminated zone formed by the beam and the gas flow path, as seen by the detector, is the view volume. The beam 20 has a characteristic changed, either by obscuration of the beam in which case the detector 21 is in line with the beam, or by scattering, in which case the detector 21 is at an angle to the axis of the beam so that only light scattered by particles is detected and not light coming directly from the laser. Gas flow cells of the type described above are illustrated in FIG. 1 of U.S. Pat. No. 4,746,215 to K. Gross.

The gas outlet port 17 is connected to an optional particle filter 26 which feeds gas to rotor chamber 25 which acts as a pump, pulling gas through the gas flow cell from the gas inlet. Rotors in the rotor chamber are described below and are driven by a motor 27 which may be a DC motor, or alternatively an AC motor or a battery-driven motor. Motor 27 operates under control of a motor controller 29, providing a command signal indicating the speed at which motor 27 is to operate.

Gas pulled through the gas flow cell by the pump, comprised of the rotor chamber 25 and the motor 27, moves through exhaust pipe 31 and passes through flowmeter 33 before going through a particle filter 37 and into gas exhaust port 39. Flowmeter 33, operating under command of controller 35, measures output gas velocity and sends a signal back to motor controller 29 which uses the flowmeter signal for a comparison with a commanded motor speed signal delivered on line 40 from an external source. The comparison of the two signals results in an error signal which is used to continuously adjust the speed of motor 27 so that the motor will turn the rotors at a velocity so that the desired output flow rate is achieved.

A signal from counter 23 may be used to influence motor controller 29. If particle counts are too fast or too great, exceeding the capacity of the system, the flow may be slowed to allow the counter to be within an accurate measuring range. For this purpose, an output signal from counter 23 is taken along line 32 to motor controller 29.

A motor speed adjustment may be commanded on line 40 to compensate for increased loads before the motor 27, such as long or constricted outlet ports 17.

Figure 2:
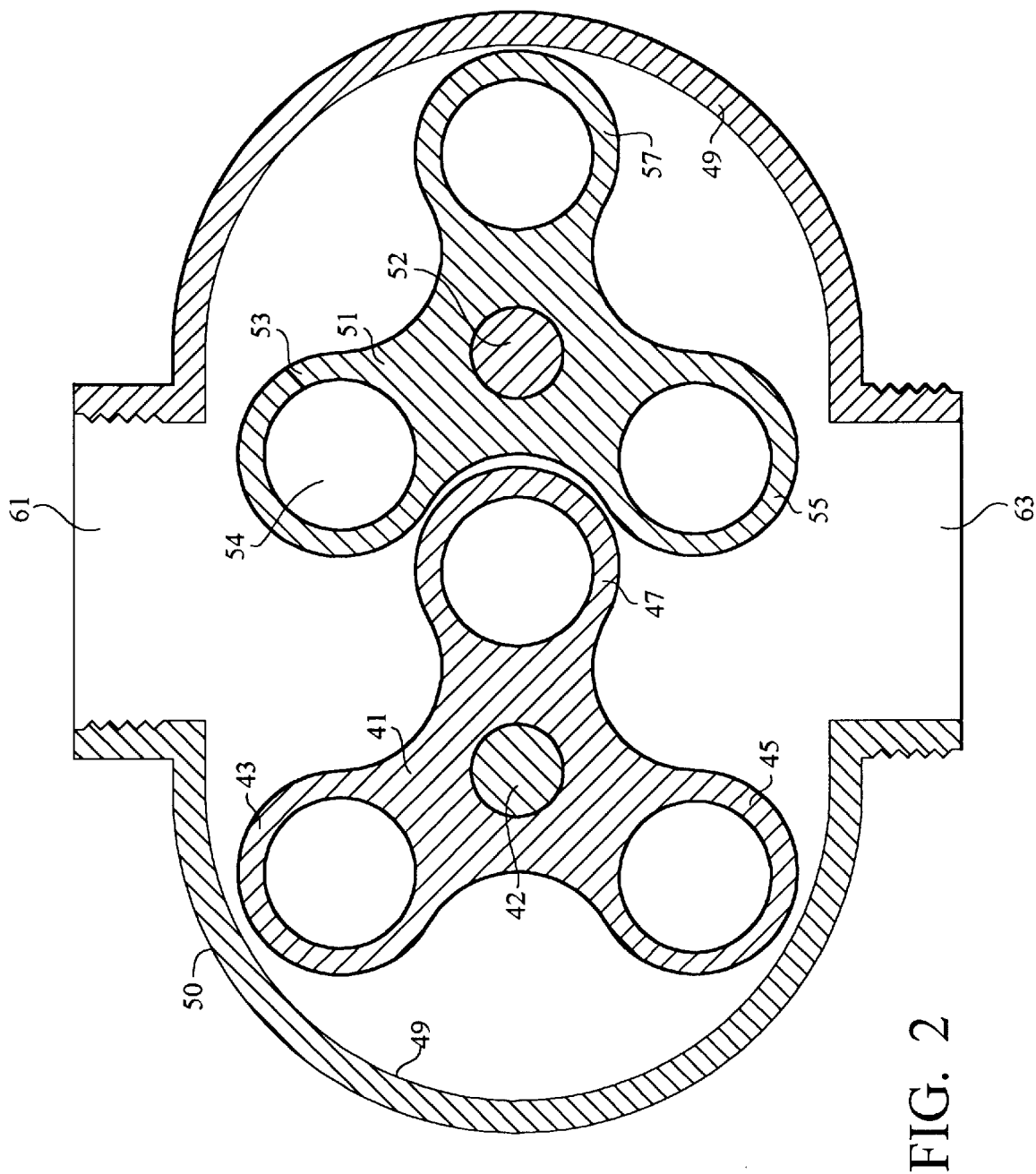
FIG. 2 is a cross section of a rotor chamber used in the apparatus of FIG. 1.

FIG. 2 shows first rotor 41 with three lobes 43, 45 and 47. These three lobes interleave with the three lobes 53, 55 and 57 of rotor 51. Note that lobe 47 does not contact lobe 53 or lobe 55 but comes in close proximity. Similarly, lobes 43, 45 and 57 come close to wall 49 of the rotor housing 50, but do not contact the wall. Rotor 41 is mounted on a central shaft 42 and rotates about the shaft, while rotor 51 is mounted on central shaft 52 and rotates about that shaft. Each of the lobes has a circular, mass-reducing cutout 54 which lowers the moment of inertia of the rotor. A motor, not shown, directly drives one of the shafts while a gear drives the second shaft and maintains synchronism. In operation, gas would be drawn in to a first port 61, connected to the gas flow cell and then be pumped out through gas outlet port 63 toward a flowmeter. The placement of the flowmeter is not important. The flowmeter could be positioned either before or after filter 37.

Figure 3:
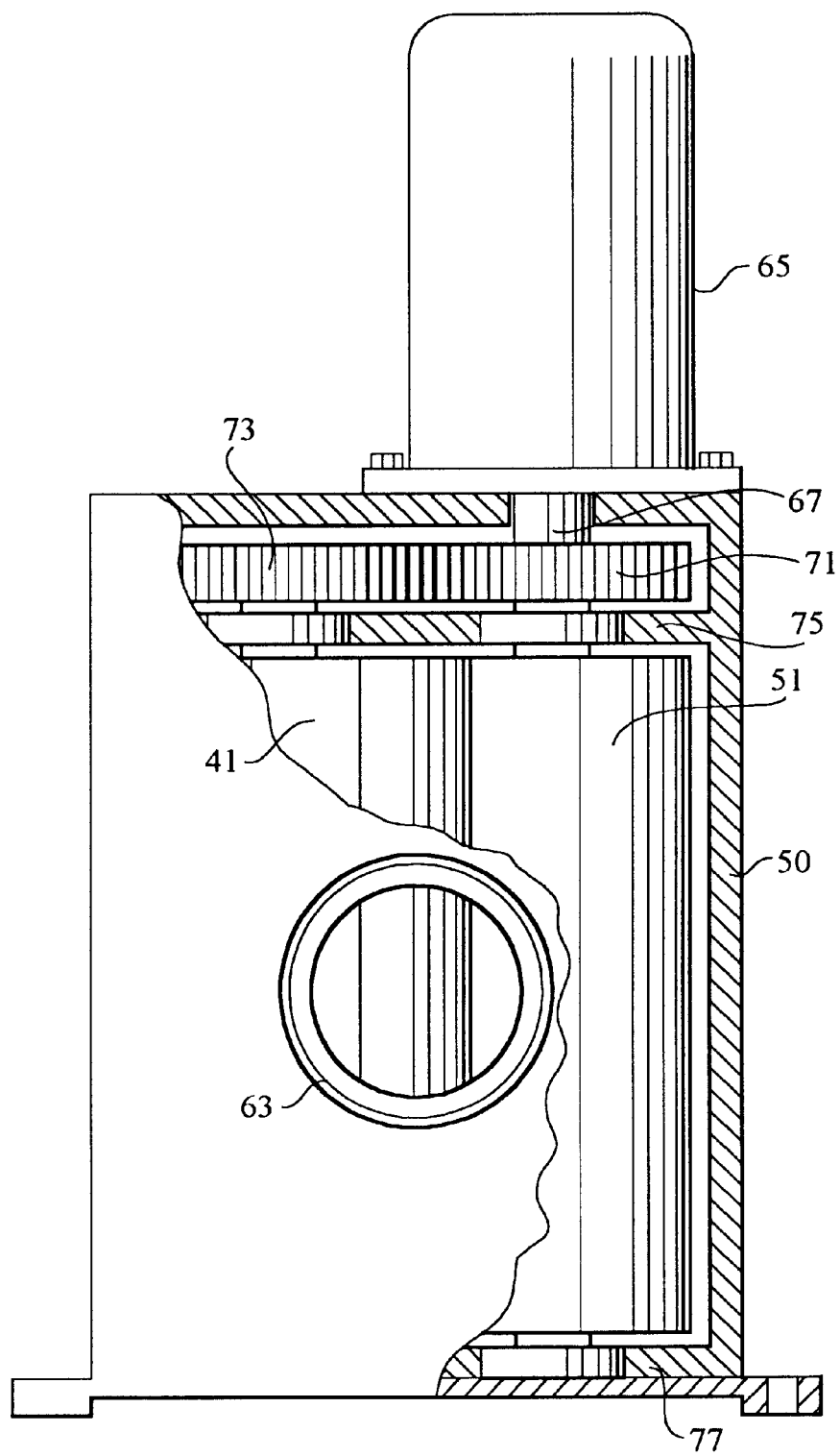
FIG. 3 is a cutaway view of a rotor chamber and motor as illustrated in FIG. 1.

In FIG. 3, motor 65 may be seen to have a shaft 67 directly turning rotor 51, as well as a first gear 71. The first gear 71 meshes with a second gear 73 which turns rotor 41 in synchronism with rotor 51. Motor 65 is preferably a DC motor which can operate off of a battery or an AC supply having a rectifier converting local AC to DC at the appropriate voltage. Operation with DC allows the pump of the present invention to be portable or to use AC as a backup supply.

Housing 50 is airtight except for a gas inlet port and a gas outlet port 63. The lobes 41 and 51 extend the full height of housing 50 which is typically only a few inches tall, with the first rotor 41 and second rotor 51 being mounted totally within the housing and supported by bearing support walls 75 and 77. The bearings are sealed units so that no particles enter the gas flow stream from bearing wear.

Figure 4:
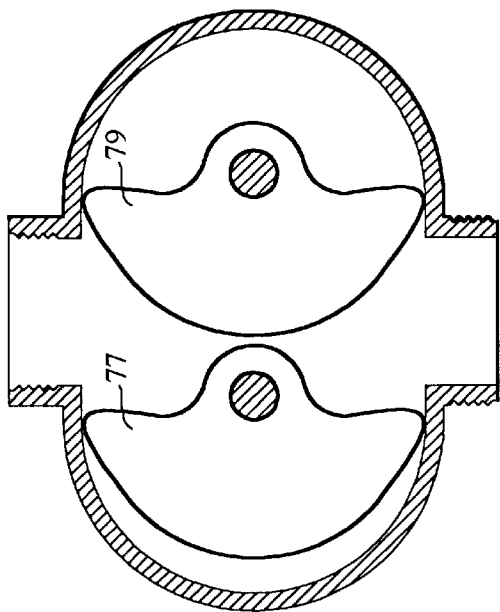
FIGS. 4–7 are alternate embodiments of lobe type rotors for use in the rotor chamber illustrated in FIG. 1.
Figure 5:
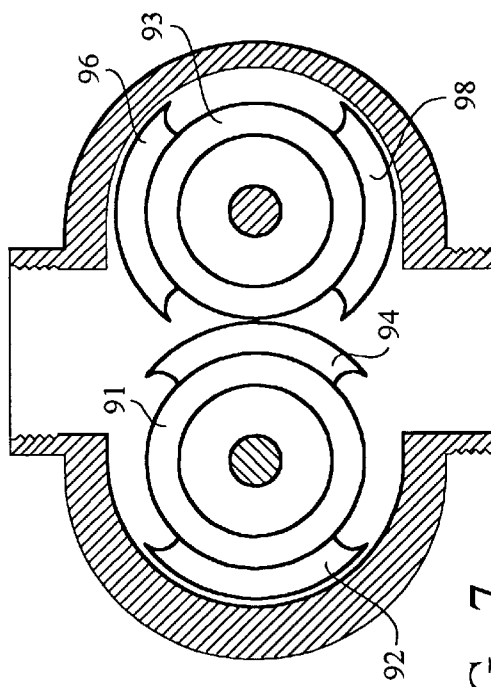

FIG. 4 shows twin lobe rotors featuring first rotor 71 and second rotor 73 within housing 75. The rotors interleave in a non-contacting way as described above. Similarly, in FIG. 5 the rotors 77 and 79 have a single lobe for each rotor with a cam-like surface. The two rotors rotate in synchronism, without contact.

Figure 6:
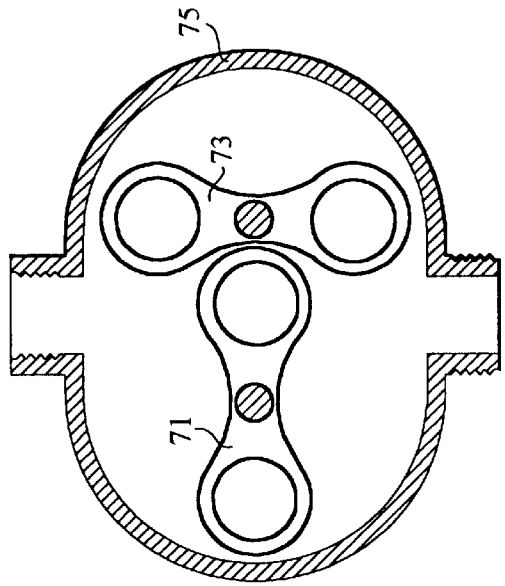

FIG. 6 shows two three-lobe rotors 83 and 85, supported on two shafts in a manner similar to the two rotors illustrated in FIG. 2. In the case of FIG. 6, the rotors have solid cross-section and a slightly different shape from that of the rotors illustrated in FIG. 2. The lobes contact neither other lobes nor housing wall surfaces.

Figure 7:
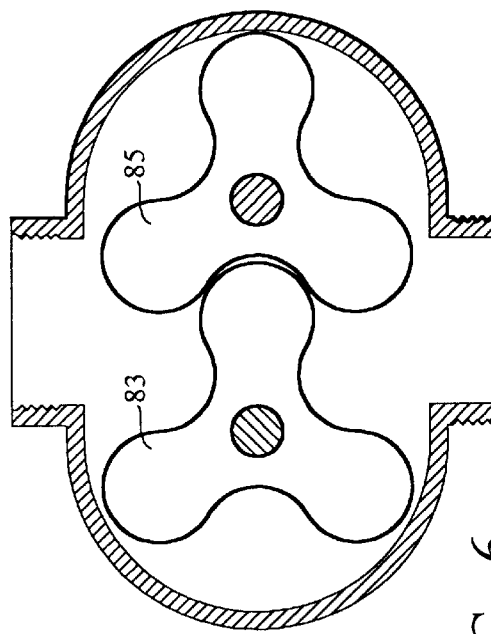

In FIG. 7, two circumferential rotors 91 and 93 are shown. Although the two rotors do not technically employ lobes, the circumferential protrusions 92 and 94 associated with rotor 91 and the circumferential protrusions 96 and 98 associated with rotor 93 may be considered to be lobes for purposes of this invention. Rotating characteristics are similar, with no contact among the lobes nor the housing wall surface.

The pumps of the present invention, resembling Roots pumps, are ideal movers of a gas flow stream in a particle counter, reducing noise, increasing efficiency and being operable by a wide variety of motors.

I claim:

1. In a particle counter of the type having a gas flow path extending through a volumetric space illuminated by a beam of light that is obscured or scattered by particles in a flowing stream of gas in the flow path wherein the obscured or scattered light is indicative of a particle count, the improvement comprising:

a multi-lobe type pump including a pump housing of efficient compact size and having inner walls within which are set a plurality of rotatable shafts, each shaft having at least one lobe interleaving with a lobe on another shaft in a noncontacting manner in gas flow communication with the volumetric space, the rotatable shafts being set in the pump housing to provide clearance between the lobes and the inner walls to prevent spurious introduction of particles into the flowing stream of gas, and the pump housing having a height not exceeding a few inches and along which the lobes substantially entirely extend.

2. The apparatus of claim 1 further comprising, a flowmeter positioned to measure the flowing stream of gas through the volumetric space, the flowmeter generating an electrical signal representing flow velocity of the flowing stream.

3. The apparatus of claim 2 further comprising, a motor operating the lobe pump and having a motor controller adjusting flow velocity through the volumetric space to a desired flow velocity represented by an electrical signal.

4. The apparatus of claim 3 further comprising, an electrical feedback circuit receiving the electrical signal representing flow velocity and the electrical signal representing the desired flow velocity, the feedback circuit generating an error signal by comparing the flow velocity and the desired flow velocity, the error signal transmitted to the motor controller thereby adjusting the flow velocity through the volumetric space.

5. The apparatus of claim 3 wherein the particle counter has a particle count capacity and the motor controller receives an input signal from the particle counter indicating whether a number of particle counts exceeds the capacity.

6. The apparatus of claim 1 wherein each shaft carries at least two lobes.

7. The apparatus of claim 1 wherein each shaft carries three lobes.

8. The apparatus of claim 1 wherein each shaft carries circumferential lobes.

9. The apparatus of claim 1 wherein the pump is positioned in a first housing that is in air flow communication with a second housing defining the volumetric space.

10. The apparatus of claim 1 further comprising, a filter disposed in the gas flow path between the pump and the volumetric space.

11. In a particle counting system for counting gas-borne particles carried by a sample stream of gas delivered to the system, the system including a gas flow cell through which the sample stream flows along a gas flow path and which receives from a light source a light beam that traverses the flow path in a volumetric space, interacts with the particles carried by the sample stream in the volumetric space, and after particle interaction impinges on a light detector, the light detector detecting the presence of scattered light or obscured light to quantify a number of particles present in the sample stream, a method of efficiently generating through the flow cell a particle-carrying sample stream of gas substantially in the absence of noise effects stemming from flow and pressure disturbances and externally generated thermal effects to accurately count the particles present in the sample stream delivered to the particle counter, comprising:

implementing the delivery of the sample stream to the particle counting system with the use of a multi-lobe type pump, the pump comprising a pump housing having inner walls within which are set multiple rotatable shafts, each having at least one lobe interleaving with a lobe of another of the multiple rotatable shafts in a noncontacting manner in gas flow communication with the volumetric space, the rotatable shafts being set in the pump housing to provide clearance between the lobes and the inner walls to prevent spurious introduction of particles into the sample stream, and the rotation of the shafts generating flow and pressure disturbances in insufficient amounts to alter the quantification of the counted particles of the sample stream as it passes through the volumetric space.

12. The method of claim 11 wherein the shafts are driven at selectable speeds of rotation by an electric motor controller, further comprising:

positioning a flowmeter to measure flow of the sample stream through the volumetric space and to generate an electrical signal representing a flow velocity of the sample stream; and providing a feedback path carrying the electrical signal from the flowmeter to the electric motor controller to regulate the speed of rotation of the rotatable shafts.

13. The method of claim 11 wherein the pump housing is of compact size and has a height, and each of the lobes extends substantially the entire height of the pump housing.

14. The method of claim 13 wherein the pump housing is of efficient compact size the height of which does not exceed a few inches.

15. The method of claim 11 wherein the light detector comprises an array detector.

* * * * *